(12) United States Patent
Patel et al.

(10) Patent No.: US 7,083,973 B2
(45) Date of Patent: Aug. 1, 2006

(54) STEREOSELECTIVE REDUCTION OF SUBSTITUTED OXO-BUTANES

(75) Inventors: Ramesh N. Patel, Bridgewater, NJ (US); Linda Chu, East Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 493 days.

(21) Appl. No.: 10/661,893

(22) Filed: Sep. 12, 2003

(65) Prior Publication Data
US 2004/0058431 A1  Mar. 25, 2004

Related U.S. Application Data

(63) Continuation of application No. 09/909,684, filed on Jul. 20, 2001, now abandoned.

(60) Provisional application No. 60/277,531, filed on Mar. 21, 2001, provisional application No. 60/225,695, filed on Aug. 16, 2000.

(51) Int. Cl.
*C12S 13/00* (2006.01)
*C12P 7/04* (2006.01)
*C12P 7/22* (2006.01)

(52) U.S. Cl. .................. 435/280; 435/157; 435/156; 435/252.1

(58) Field of Classification Search .............. None
See application file for complete search history.

(56) References Cited

U.S. PATENT DOCUMENTS

| 5,391,495 A | 2/1995 | Patel et al. |
| 5,849,911 A | 12/1998 | Fassler et al. |

FOREIGN PATENT DOCUMENTS

| JP | A-61-108394 | 5/1986 |
| JP | A-2-295969 | 12/1990 |
| JP | A-2-295970 | 12/1990 |
| JP | A-9-285 | 1/1997 |
| JP | A-9-289897 | 11/1997 |
| JP | A-11-103878 | 4/1999 |

OTHER PUBLICATIONS

Zhou et al. (1983) Journal of American Chemical Society, vol. 105, pp. 5926-5928.
Kazutoshi et al. (1986) Tetrahedron Letters, vol. 27, No. 23, pp. 2657-2660.
Christen et al. (1988) Journal of Chem. Soc., Chem. Comm., pp. 264-266.
Tricone et al. (1990) Biotechnology and Bioengineering, vol. 35, pp. 559-564.
Patel et al. (1991) Enzyme Microb. Technology, vol. 13, pp. 906-912.
Patel et al. (1993) Enzyme Microb. Technology, vol. 15, pp. 1014-1021.
Patel et al. (1992) Enzyme Microb. Technology, vol. 14, pp. 731-738.
Kometani et al. (1995) Journal of Fermentation and Bioengineering, vol. 80, No. 2, pp. 208-210.
A. Albeck, et al, "Functionalized *Erythro* N-Protected α-Amino Epoxides. Stereocontrolled Synthesis and Biological Activity," Tetrahedron, 53(14), pp. 5325-5338, 1997.
R.N. Patel, "Biocatalytic Synthesis of Chiral Intermediates for Antiviral and Antihypertensive Drugs," Journal American Oil Chemical Society, 76(11), pp. 1275-1281, 1999.

*Primary Examiner*—Irene Marx
(74) *Attorney, Agent, or Firm*—Samuel J. DuBoff; Warren K. Volles

(57) ABSTRACT

The present invention relates to a process for the stereoselective enzymatic reduction of 1-halo-2-oxo-3-(protected) amino-4-substituted-butanes utilizing certain species of *Rhodococcus* and *Brevibacterium*. The product 1-halo-2-hydroxy-3-(protected)amino-4-substituted-butanes, which are useful as intermediates in the synthesis of compounds that are inhibitors of ACE, renin and HIV proteases, are obtained in high yield and, particularly, in very high diastereomeric purity. The process is advantageously highly selective for the (3S,2R) enantiomer of the product.

14 Claims, No Drawings

STEREOSELECTIVE REDUCTION OF SUBSTITUTED OXO-BUTANES

CROSS-REFERENCE TO RELATED APPLICATIONS

This application is a continuation of U.S. patent application Ser. No. 09/909,684, filed Jul. 20, 2001 now abandoned and claims the benefit of U.S. Provisional Application Ser. No. 60/277,531 filed Mar. 21, 2001 and 60/225,695 filed Aug. 16, 2000.

FIELD OF THE INVENTION

The present invention relates to a novel process for the preparation of (3S,2R)-1-halo-2-hydroxy-3-(protected) amino-4-substituted butanes by stereoselective reduction of the corresponding oxo compounds. The substituted butanes produced in accordance with the process of the inventions are precursors of hydroxyethylamine isostere sub-units present in many molecules therapeutically useful as inhibitors of angiotensin converting enzyme, renin and HIV-protease.

BACKGROUND OF THE INVENTION

Bing-nan Zhou et al. *J. Am Chem. Soc.*, 105, pages 5926–5928, 1983 describe the chemomicrobiological synthesis of L-carnitine, which plays an important role in the human metabolism and transport of long-chain fatty acids. Particularly, this paper teaches the reduction by baker's yeast, i.e. *Saccharomyces cerevisiae*, of ethyl K-chloroacetoacetate to ethyl (S)-4-chloro-3-hydroxybutanoate.

Kazutoshi Ushio et al. *Tetrahedron Letters*, Vol. 27, No. 23, pages 2657–2660, 1986, disclose the reduction of beta-keto esters by methanol grown yeast. This paper teaches that the subject reaction causes dramatic shifts of the enantiomer excess of the resultant product in the direction of the D-isomer. This phenomena was produced when the reaction was carried out utilizing yeast grown in methanol due to enzymes characteristic of yeast grown in such media.

Markus Christen et al. *J. Chem. Soc., Chem. Commun.* pages 264–266, 1988, discloses the synthesis of four stereoisomers of methyl-6-(p-chlorophenylthio)-3,4-dihydrohexanoate in which the key introduction of chirality was effected by an appropriate yeast reduction. It is stated therein that, although the reduction of beta-keto esters with yeast has been studied extensively, it remains difficult to predict either the absolute configuration of the product(s) or, in particular, the enantiomeric excess likely to be achieved.

Antonio Trincone et al., *Biotechnology and Bioengineering*, Vol. 35, pages 559–564, 1990 describe asymmetric reduction of ketones with resting cells of *Sulfolobus solfataricus*. It is stated that the reductive ability of the resting cells of this organism strongly depends on the phase of cell growth.

Ramesh Patel et al., *Enzyme Microb. Technol.*, Vol. 13, pages 906–912, 1991 describe the stereospecific microbial reduction of 4,5-dihydro-4-(4-methoxyphenyl)-6-(trifluoromethyl-1H-1)-benzazepin-2-one. In particular, it is disclosed that a key intermediate (3R-cis)-1,3,4,5-tetrahydro-3-hydroxy-4-(4-methoxyphenyl)-6-(trifluoromethyl)-2H-1-benzazepine-2-one was made by the stereoselective microbial reduction of the parent ketone. It is stated that it was possible by the selection of specific conditions to obtain a single isomer from among four known possibilities.

Ramesh Patel et al., *Enzyme Microb. Technol.*, Vol. 15, pages 1014–1021, 1993, describes the stereoselective reduction of a diketo compound, 3,5-dioxo-6-(benzyloxy) hexanoic acid, methyl ester, to a single enantiomer of the resulting dihydroxy compound.

Ramesh Patel et al., *Enzyme Microb. Technol.*, Vol. 14, pages 731–738, 1992, describe a process of heat treating *Geotrichum candidum* to improve the optical purity of the hydroxy product obtained from the reduction of beta-keto esters thereby.

Kometani et al., *Journal of Fermentation and Bioengineering*, Vol. 80, No. 2, pages 208–210, 1995, teaches yeast-mediated bioreduction utilizing ethanol as the energy source. The relationship between the rate of consumption of ethanol and the prochiral ketone reduction rate in Baker's Yeast is examined and it is concluded that ethanol could be applicable to large-scale production of chiral alcohols from prochiral ketones.

Ramesh Patel et al., U.S. Pat. No. 5,391,495, issued Feb. 21, 1995, discloses the stereoselective reduction of certain keto-containing sulfonamide compounds to form the corresponding hydroxyl group-containing compounds utilizing a microorganism or an enzyme capable of catalyzing the reduction. The enzymes named are oxido-reductase or dehydrogenase and the microorganisms are preferably selected from *Hansenula, Rhodococcus* and *Norcardia* species.

SUMMARY OF THE INVENTION

The present invention is directed to a novel stereoselective process for the preparation of (3S,2R)-1-halo-2-hydroxy-3-(protected)amino-4-substituted butanes by the reduction of the corresponding keto group containing compounds by certain species of *Rhodococcus* and *Brevibacterium*. The products are obtained in high yield and in excellent diastereomeric purity.

DETAILED DESCRIPTION OF THE INVENTION

The process of the present invention provides an advantageous synthesis for the (3S,2R)-1-halo-2-hydroxy-3-(protected)amino-4-substituted butanes represented by the formula

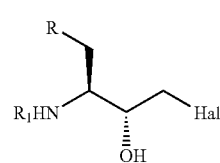

I wherein Hal is a halogen, preferably chlorine, R is selected from the group consisting of alkyl, substituted alkyl, aryl and substituted aryl and $R_1$ is a protecting group for the amino function.

The substituted butanes represented by formula I are useful as intermediates in the synthesis of molecules that are inhibitors of ACE, renin and HIV proteases. The activity of such molecules against HIV proteases makes them very valuable in the treatment of retroviral infections such as AIDS. Such compounds and their use are disclosed, for example, in U.S. Pat. No. 5,849,911, the disclosure of which is incorporated herein by reference. A particularly important AIDS compound disclosed in U.S. Pat. No. 5,849,911 is [3S-(3R*,8R*,9R*,12R*)]-3,12-Bis(1,1-dimethylethyl)-8-hydroxy-4,11-dioxo-9-(phenylmethyl)-6{[4-(2-pyridinyl) phenyl]methyl}-2,3,6,10,13-pentaazaretetradecanedioic acid dimethyl ester. This compound may be directly synthesized from the (3S,2R)-1-halo-2-hydroxy-3-(protected) amino-4-substituted butanes represented by formula I. The fact that the process of the present invention produces a very high yield of the trans (3S,2R) enantiomer of the substituted butanes represented by formula I makes it very important to the ultimate efficiency of the synthesis of the therapeutic compound described above.

As utilized herein, the following terms have the definitions given below. The term "alkyl" refers to optionally substituted straight- or branched-chain saturated hydrocarbon groups having from 1 to 7 carbon atoms, preferably from 1 to 4 carbon atoms. The expression "lower alkyl" refers to optionally substituted alkyl groups having from 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryl, aryloxy, aralkyl, alkanoyloxy, amino, alkylamino, arylamino, aralkylamino, cycloalkylamino, heterocycloamino and disubstituted amino. The definitions given herein for alkyl and substituted alkyl apply as well to the alkyl portion of alkoxy groups.

The term "aryl" refers to monocyclic or bicyclic aromatic hydrocarbon groups having from 6 to 12 carbon atoms in the ring portion, for example, phenyl, naphthyl, biphenyl and diphenyl groups, each of which may be substituted.

The term "aralkyl" refers to an aryl group bonded to a larger entity through an alkyl group, for example, a benzyl radical.

The term "substituted aryl" refers to an aryl group substituted by, for example, one to four substituents such as alkyl; substituted alkyl, halo, trifluoromethyl, trifluoromethoxy, hydroxy, alkoxy, cycloalkyloxy, heterocyclooxy, alkanoyl, alkanoyloxy, amino, alkylamino, dialkylamino, aralkylamino, cycloalkylamino, heterocycloamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by one or more members selected from the group consisting of halo, hydroxy, alkyl, alkoxy, aryl, substituted alkyl, substituted aryl and aralkyl.

The term "halogen" or "Hal" refers to chlorine, bromine, fluorine and iodine, with chlorine being preferred.

The term "protecting group on the amino function" refers to an art-recognized group of moieties that can be attached to an amino group to keep it from being involved in reactions taking place elsewhere on the molecule to which it is attached. Preferred among such groups is t-butoxycarbonyl (BOC), but art-recognized amino function protecting groups, generally alkoxycarbonyl groups such as benzyloxycarbonyl, can be used as well.

The starting materials for the process of subject process for preparing the (3S,2R) -1-halo-2-hydroxy-3-(protected) amino-4-substituted butanes represented by formula I are the corresponding keto group-containing compounds represented by the formula

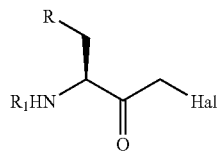

wherein Hal, R and $R_1$ are as defined above. The compounds represented by formula II can be prepared by techniques described in the literature and known to those of ordinary skill in the art. A preferred process for forming the compounds represented by formula II is disclosed in co-pending patent application U.S. Ser. No. 09/908,516, filed Jul. 18, 2001, the disclosure of which is incorporated herein by reference. In this method, an aryl ester represented by the formula

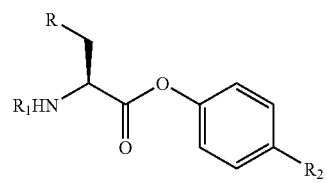

wherein R and $R_1$ are as defined above and $R_2$ is hydrogen or nitro and may be substituted in the ortho or para position on the phenyl ring is reacted with a sulfur ylide, i.e. a compound containing a function represented by the formula

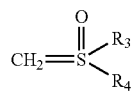

to produce an intermediate keto ylide compound represented by the formula

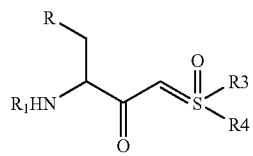

wherein R and $R_1$ are as defined above and $R_3$ and $R_4$ are selected from the group consisting of alkyl, substituted alkyl and aryl. The keto ylide compound represented by the above formula is then converted to the keto group-containing compounds represented by formula II by reaction with a source of chloride, preferably a basic source of chloride, most preferably lithium chloride, and an organic acid, for example, methanesulfonic acid.

The (3S,2R)-1-halo-2-hydroxy-3-(protected)amino-4-substituted butanes represented by formula I above are important intermediates of in the synthesis of molecules that are inhibitors of ACE, renin and HIV proteases. The activity of such molecules against HIV proteases makes them very valuable in the treatment of retroviral infections such as AIDS. Specifically, the (3S,2R)-1-halo-2-hydroxy-3-(protected)amino-4-substituted butanes represented by formula I are treated with a suitable base to convert them to the corresponding epoxides represented by the formula shown below

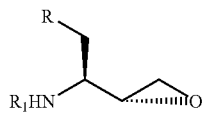

The epoxide compounds represented by formula shown above are intermediates that can be converted to the important AIDS compound [3S-(3R*,8R*,9R*,12R*)]-3,12-Bis(1,1-dimethylethyl)-8-hydroxy-4,11-dioxo-9-(phenylmethyl)-6{[4-(2-pyridinyl)phenyl]methyl}-2,3,6,10,13pentaazaretetradecanedioic acid dimethyl ester as disclosed in U.S. Pat. No. 5,849,911, the disclosure of which is incorporated herein by reference.

The stereoselective reduction of the (3S)-1-halo-2-oxo-3-(protected)amino-4-substituted butanes represented by formula II above to form the (3S,2R)-1-halo-2-hydroxy-3-(protected)amino-4-substituted butanes represented by formula I is carried out in accordance with the present invention by reaction with an oxidoreductase enzyme, or preferably, a microorganism that supplies an oxidoreductase enzyme capable of catalyzing the enzymatic reduction of the ketones represented by formula II. The cells of the microorganism may be in the form of intact wet cells or dried cells such as lyophilized, spray-dried or heat-dried cells, or in the form of treated cell material such as ruptured cell or cell extracts. While a large and varied number of microorganisms are known to supply some form of oxidoreductase, it has been found in accordance with the present invention that only selected species of *Rhodococcus* and *Brevibacterium* catalyze the reduction of the compound represented by formula II to form the desired (3S,2R)-1-halo-2-hydroxy-3-(protected)amino-4-substituted butanes in high quantitative and enantiomeric yield. These species are *Rhodococcus erythropolis* ATCC 4277, *Rhodococcus erythropolis* DSM 6971 and *Rhodococcus* sp. ATCC 21227, *Rhodococcus erythropolis* ATCC 27854 and *Brevibacterium* sp. ATCC19653. The term "ATCC" as used herein refers to the accession number of the depository for the particular organism, i.e. the American Type Culture Collection, 12301 Parklawn Drive, Rockville, Md. 20852. The term "DSM" refers to the German Collection of Microorganisms and Cell Cultures, Branschweig, Germany.

The enzymatic reduction method of the present invention may be carried out subsequent to the fermentation of the microorganism employed, i.e. as a two-stage fermentation and reduction, or concurrently therewith, i.e. as a single-stage or in situ fermentation and reduction. In the latter, the microorganism may be grown in an appropriate medium, especially one containing nitrogen and carbon sources, until sufficient growth is realized and then a compound selected from those compounds represented by formula II is added thereto. The enzymatic reduction is thereafter continued until virtually complete conversion of the compound represented by formula II is attained.

In the two-stage methodology, the microorganism is initially grown in a suitable medium as described above until it exhibits a predetermined level of enzymatic activity at which point the cells are harvested by conventional separation techniques and microbial cell suspensions prepared therefrom containing appropriate buffering agents and the like. Suitable buffering agents include phosphate buffers, particularly potassium phosphate buffer, tris-HCl, sodium acetate and the like. Water may also be used to prepare suspensions of microbial cells. The compound represented by formula II is then added thereto and the enzymatic reduction continued until the conversion is virtually complete. In either instance, the appropriate growth medium will include, as previously stated, sources of carbon and nitrogen and trace elements. Inducers may be added as well. As those of ordinary skill in the art are aware, the term inducer means any compound initiating or enhancing the desired enzymatic, i.e. oxidoreductase, activity within the cell to produce the desired product. The (3S)-1-halo-2-oxo-3-(protected)amino-4-substituted butanes represented by formula II would be considered an inducer, particularly when added in small quantities during the growth of the microorganism.

Suitable carbon sources for the medium may include sugars, such as maltose, lactose, glucose, fructose, glycerol, sorbitol, sucrose, starch, mannitol, propylene glycol and the like, organic acids and their salts such as sodium acetate, sodium citrate and the like, amino acids and their salts, such as sodium glutamate and the like, and alcohols, such as ethanol, propanol and the like. Suitable nitrogen sources may include N-Z amine A, corn steep liquor, soy bean meal, beef extracts, yeast extracts, molasses, baker's yeast, tryptone, nutrisoy, peptone, yeastamin, sodium nitrate, ammonium sulfate and the like. Suitable trace elements may include phosphates, and magnesium, manganese, calcium, cobalt, nickel, iron, sodium and potassium salts. The appropriate media utilized in accordance with the present invention may include a plurality of constituents selected from any of these categories. Representative preferred media include without intended limitation aqueous media containing the following, in weight percent:

|  | Ingredient | Weight Percent |
| --- | --- | --- |
| No. 1 | Malt Extract | 1% |
| pH 7.0 | Yeast Extract | 1% |
|  | Peptone | 1% |
|  | Glucose | 2% |
| No. 2 | Malt Extract | 1% |
| pH 7.0 | Yeast Extract | 1% |
|  | Peptone | 0.3% |
|  | Glucose | 4% |
| No. 3 | Malt Extract | 1% |
| pH 7.0 | Yeast Extract | 1% |
|  | Peptone | 0.3% |
|  | Glucose | 2% |
| No. 4 | Malt Extract | 1% |
| pH 7.0 | Yeast Extract | 1% |
|  | Peptone | 0.3% |
|  | Sodium Succinate | 2% |

The pH given above for the media is post-sterilization. Before sterilization, the pH is preferably adjusted to from about 6 to 8, most preferably about pH 6.5. The media are then sterilized, for example, by heating at a temperature of about 121° C. for 30 minutes. Following sterilization, the media are adjusted to pH 6.5 to 7.5, most preferably about pH 7.0. During microbial growth and the reduction process, the pH is maintained at between about 4.0 and 9.0, preferably between about pH 6.0 and 8.0. An appropriate base or acidic salt from among the constituents named above can conveniently be utilized for adjustment of the pH.

The temperature of the reaction mixture is a measure of the heat energy available for the reduction process, and for this reason, a suitable temperature should be maintained to ensure that there is sufficient energy available for the process to go to completion. A suitable temperature range for the process of the invention is in the range of from about 15° C. to about 60° C., preferably from about 25° C. to about 40° C. Pressure is not known to be critical for the practice of the process of the invention and for convenience about atmospheric pressure is typically maintained.

The process of the present invention is preferably carried out under aerobic conditions. Agitation and aeration of the reaction mixture is also beneficial to the subject process in that is affects the amount of oxygen available for the biotransformation. The process is advantageously carried out, for example, in shake-flask cultures or fermentor tanks during the growth of the microorganisms in a single-stage or two-stage process as described above. Agitation in the range of from about 50 to 1000 RPM is preferred, with from about 50 to 500 RPM being most preferred. Aeration of from about 0.1 to 10 volumes of air per volume of media per minute (v/Vt.) is preferred, with aeration of about 5 volumes per volume of media per minute being particularly preferred.

Complete conversion of the compound represented by formula II may require, for example, from about 4 to 48 hours, typically from about 4 to 24 hours, measured from the time of addition of the compound represented by formula II to the media. It is preferred that the media be aqueous based, although an organic liquid or a miscible or immiscible, i.e. biphasic, organic/aqueous liquid mixture may be utilized as well.

The stereoselective enzymatic reduction process of the present invention may be carried out using a co-factor such as nicotinamide adenine dinucleotide (NADH), especially when an isolated enzyme would be utilized. NADH, for example, may thereafter be regenerated and reused. A further enzyme that regenerates the NADH in situ may be employed such as formate dehydrogenase or glucose dehydrogenase. Suitable hydrogen donors include molecular hydrogen, a formate (e.g. an alkali metal or ammonium formate), glucose, a hypophosphite or an electrochemical reduction in the presence of a viologen, for example methyl viologen. It is also possible to regenerate NADH without further enzymes using, for example, ethanol or formate. It is further preferred to add the compound of formula II to the reaction media so that it is from about 0.2% to about 5% by weight, based on the combined weight of starting compound and media. The inoculum of microorganism relative to the amount of starting material is sufficient to provide for the enzymatic reduction of the compound represented by formula II with the times described above, generally from about 5 wt. % to about 30 wt. % cells concentration. Utilizing the preferred reaction parameters described above with the microorganisms given will provide a reaction yield of greater than 70%, optimally in excess of 99% and, unexpectedly, an diastereomeric purity greater than 93%, optimally in excess of 99% of the desired enantiomer of the compound represented by formula I. The product of the reduction process of the present invention, i.e. the compounds represented by formula I may be recovered by any suitable methods for isolation and/or purification, e.g. methodologies such as extraction, distillation, crystallization, column chromatography and the like.

It is understood that various other embodiments and modifications in the practice of the invention will be apparent to, and can be readily made by, those of ordinary skill in the art without departing form the scope and spirit of the invention as described above. Accordingly, it is not intended that the scope of the claims appended hereto be limited to the exact description set forth above, but rather that the claims be construed as encompassing all of the features of patentable novelty that reside in the present invention, including all the features and embodiments that would be treated as equivalents thereof by those skilled in the relevant art. The invention is further described with reference to the following experimental work.

EXAMPLE 1

Stereoselective Enzymatic Reduction: Use of Whole Cells—Single Stage Process

*Rhodococcus erythropolis* ATCC 4277 cells (1 mL) was inoculated into 100 mL of Medium 1 as noted above in a 500 mL flask and incubated at 28° C. and 200 RPM on a shaker for 22 hours. The pH of 50 cells broth was adjusted to pH 7.0 with 1 M potassium phosphate buffer. Glucose was added to the cell broth at 25 mg/mL and 50 mg. of (1S)-[N-(1-benzyl-2-oxo-3-chloro)propyl]carbamic acid t-butyl ester (the substrate) was added thereto. The biotransformations (reductions) were carried out at 28° C. and 200 RPM on a shaker. At predetermined times the reaction mixtures were quenched with two volumes of a 60:40 mixture of t-butyl methyl ether and toluene, and the separated organic phase was filtered through a 0.2 micron filter and collected. Two mL of the organic phase was evaporated to dryness under a stream of nitrogen and the residue taken up with 1 mL of acetonitrile, filtered and analyzed by HPLC for (1S,2R)-[N-(1-benzyl-2-hydroxy-3-chloro)propyl]carbamic acid t-butyl ester (the product). The results are summarized in Table 1 below.

TABLE 1

| Microorganism | Reaction Time (hours) | Substrate (mg./mL) | Product (mg./mL) | Diastereomeric Purity (%) |
|---|---|---|---|---|
| *Rhodococcus erythropolis* ATCC 4277 | 21 hrs | 0.45 | 0.48 | >98 |
| | 93 hrs | 0.05 | 0.95 | >98 |

EXAMPLE 2

Use of Whole Cells: Two Stage Process

The substrate and the product for this Example were as described in Example 1. Cells of *Rhodococcus erythropolis* ATCC 4277 and *Rhodococcus erythropolis* DSM 6971 (1 mL) were individually inoculated into 100 mL portions of Medium 1 as noted above in a 500 mL flask and incubated at 25° C. and 280 RPM on a shaker for 48 hours. One hundred m.L of each culture was innoculated into 15 mL of Medium 1 combined in a fermentor. Growth in the fermentor was carried out at 25° C., 15 LPM (liters per minute) aeration and 500 RPM agitation for 36 hours. Cells were harvested from the fermentor and used for the enzymatic conversion (biotransformation) of (1S)-[N-(1-benzyl-2-oxo-3-chloro)propyl]carbamic acid t-butyl ester (the substrate) to (1S,2R)-[N-(1-benzyl-2-hydroxy-3-chloro)propyl]carbamic acid t-butyl ester (the product). Cell suspensions were prepared by suspending the cells, 20 grams in 100 mL of 64 mM potassium phosphate buffer, pH 7.0. To each suspension was added 25 mg/mL of glucose and a predetermined concentration of substrate. The biotransformation of the substrate to the product was carried out at 28° C. and 160 RPM on a shaker. At predetermined times the reaction mixtures were quenched and the product obtained and analyzed as described in Example 1. The results are summarized in Table 2 below.

TABLE 2

| Microorganism | Reaction Time (hrs) | Substrate Used (mg/mL) | Substrate (mg/mL) | Product (mg/mL) | Diastereomeric Purity (%) |
|---|---|---|---|---|---|
| Rhodococcus erythropolis ATCC 4277 | 20 | 1.0 | 0 | 0.86 | >98 |
| | 32 | 5 | 0.02 | 4.9 | >98 |
| | 49 | 10 | 0.05 | 9.65 | >98 |
| Rhodococcus erythropolis DSM 6971 | 20 | 1 | 0 | 0.95 | >98 |
| | 24 | 5 | 0 | 4.83 | >98 |
| | 46 | 10 | 0 | 9.2 | >98 |

The results in Tables 1 and 2 demonstrate that the desired product is obtained by the process of the invention in high yield and with a very high diastereomeric purity.

EXAMPLE 3

Use of Various Microbial Strains for Biotransformation: Whole Cells

A series of microorganisms was utilized to carry out the biotransformation according to the process of Example 1. The results are shown in Table 3.

TABLE 3

| Microorganism | Culture ID | Substrate Input (mg/mL) | Yield (%) | Diastereomeric Purity (%) |
|---|---|---|---|---|
| Agrobacterium tumifaciens | ATCC 33970 | 1 | 25.4 | 75.8 |
| Brevibacterium sp. | ATCC 19653 | 2 | 100 | 93.9 |
| Hansenula anomala | ATCC 8170 | 1 | 31.8 | 76.2 |
| Hansenula anomala | ATCC 58044 | 1 | 33.1 | >98 |
| Hansenula polymorpha | ATCC 34438 | 1 | 37.6 | 79.2 |
| Hansenula polymorpha | ATCC 26012 | 1 | 6.1 | >98 |
| Hansenula saturnus | ATCC 16762 | 1 | 35.1 | >98 |
| Pseudomonas cepacia | ATCC 29351 | 1 | 5.2 | — |
| Pseudomonas species | ATCC 202027 | 1 | 5.1 | — |
| Rhodococcus erythropolis | ATCC 4277 | 2 | 74.2 | >98 |
| Rhodococcus erythropolis | ATCC 27854 | 2 | 77.7 | >98 |
| Rhodococcus erythropolis | ATCC 25544 | 2 | 61.1 | >98 |
| Rhodococcus erythropolis | DSM 6971 | 2 | 100 | >98 |
| Rhodococcus erythropolis | DSM 6977 | 2 | 72.8 | >98 |
| Rhodococcus maris | ATCC 35013 | 2 | 16.6 | >98 |
| Rhodococcus rhodococcus | ATCC 14347 | 2 | 66.2 | 61.9 |
| Rhodococcus rhodococcus | ATCC 21197 | 2 | 14.0 | — |
| Rhodococcus species | ATCC 15592 | 2 | 91.2 | >98 |
| Rhodococcus species | ATCC 29673 | 2 | 32.5 | >98 |
| Rhodococcus species | ATCC 21227 | 2 | 100 | >98 |
| Rhodococcus species | ATCC 21146 | 2 | 42.7 | >98 |
| Rhodococcus species | ATCC 19071 | 2 | 14.3 | — |
| Rhodococcus species | ATCC 21226 | 2 | 56.6 | >98 |
| Trichoderma viridae | ATCC 20536 | 1 | 12.2 | >98 |

The results in Table 3 demonstrate that the microorganisms of the invention clearly cause production of the product in acceptable yields, i.e. in excess of 70% and acceptable diastereomeric purity, i.e. in excess of 90%.

EXAMPLE 4

Use of Cell Extracts and Co-Factor

The substrate for this process and the product were as in the previous Examples. Cells of Rhodococcus erythropolis ATCC 4277 were grown on Medium 1 as described above. Cells (150 grams) were suspended in 100 mL of potassium phosphate buffer, pH 7.0. The cell suspensions were disintegrated at 4° C. by use of a microfluidizer at 13,000 psi pressure. The disintegrated cell suspension was centrifuged at 12,000 RPM for 30 minutes. The clear supernant ("cell extracts") was utilized for the biotransformation of the substrate to the product.

Portions (10 mL) of cell extract were supplemented with 10 mg of substrate, glucose dehydrogenase (35 units), 0.7 mM NAD+ (nicotinamide adenine dinucleotide) and 200 mg of glucose. The reaction was carried out in a pH stat at pH 6.0, 150 RPM agitation and 30° C. Samples were periodically withdrawn from the reaction media and analyzed. The product was obtained in 95% yield and >98% diastereomeric purity. In this example, the NADH cofactor was regenerated using glucose dehydrogenase, NAD+ and glucose as shown below.

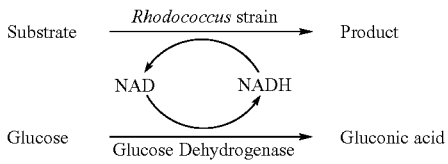

We claim:

1. A stereoselective process for the preparation of (3S, 2R)-1-halo-2-hydroxy-3-(protected)amino-4-substituted butanes represented by the formula I

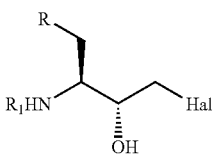

wherein Hal is halogen, R is selected from the group consisting of alkyl, substituted alkyl, aryl and substituted aryl and $R_1$ is a protecting group for the amino function comprising contacting a (3S)-1-halo-2-oxo-3-(protected) amino-4-substituted butane represented by formula II

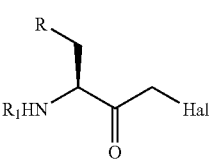

wherein Halo, R and $R_1$ are as defined above with a microorganism capable of catalyzing the stereoselective reduction of the compound represented by formula II wherein said microorganism is selected from the group consisting of Rhodococcus erythropolis ATCC 4277,

*Rhodococcus etythropolis* DSM 6971, *Rhodococcus* sp. ATCC 21227, *Rhodococcus erythropolis* ATCC 27854 and *Brevibacterium* sp. ATCC19653 under conditions such that said reduction is effected, and recovering said compound represented by formula I.

2. A process in accordance with claim 1, wherein Hal is chloro, R is phenyl and $R_1$ is t-butoxycarbonyl.

3. A process in accordance with claim 1, wherein said microorganism is *Rhodococcus erythropolis* ATCC 4277.

4. A process in accordance with claim 1, wherein said microorganism is *Rhodococcus erythropolis* DSM 6971.

5. A process in accordance with claim 1, wherein said microorganism is *Rhodococcus* species ATCC 21227.

6. A process in accordance with claim 1, wherein said microorganism is *Rhodococcus* species ATCC 27854.

7. A process in accordance with claim 1, wherein said microorganism is *Brevibacterium* sp. ATCC19653.

8. A process in accordance with claim 1 carried out as a one-stage fermentation.

9. A process in accordance with claim 1 carried out as a two-stage fermentation.

10. A process in accordance with claim 1 carried out in the presence of an inducer effective to initiate or enhance the reduction.

11. A process in accordance with claim 10, wherein the inducer is a compound represented by formula I that is added during the growth of said microorganism.

12. A process in accordance with claim 1, wherein compound represented by formula I is obtained in at least 70% yield and at least 93% diastereomeric purity.

13. A process in accordance with claim 10, wherein compound represented by formula I is obtained in at least 95% yield and at least 99% diastereomeric purity.

14. A process in accordance with claim 10, wherein the inducer is a 1-halo-2-oxo-3-(protected) amino-4-substituted butane represented by formula II.

* * * * *